United States Patent [19]

Thome et al.

[11] Patent Number: 5,470,522
[45] Date of Patent: Nov. 28, 1995

[54] METHOD OF MOLDING Y-ADAPTER WITH A SIDEPORT RADIUS

[76] Inventors: Scott P. Thome, 535 Aberdeen Dr., Waite Park, Minn. 56387; Thomas J. Holman, 2622 Idaho Ave. S., St. Louis Park, Minn. 55426

[21] Appl. No.: 273,811

[22] Filed: Jul. 12, 1994

Related U.S. Application Data

[62] Division of Ser. No. 935,856, Aug. 26, 1992, Pat. No. 5,352,215.

[51] Int. Cl.⁶ .......................... B29C 45/36; B29C 45/44
[52] U.S. Cl. .......................... 264/328.1; 264/334; 249/64; 249/145; 249/151; 425/556; 425/577; 425/438; 425/468; 425/DIG. 58
[58] Field of Search ................ 264/328.1, 334; 249/64, 145, 151; 425/556, 577, 438, 441, 468, DIG. 58; 604/284, 283

[56] References Cited

U.S. PATENT DOCUMENTS

| | | |
|---|---|---|
| 701,075 | 5/1892 | McCully . |
| 883,583 | 3/1908 | Stallsmith . |
| 998,339 | 7/1911 | Hollins . |
| 1,505,208 | 8/1924 | Larner . |
| 2,308,484 | 1/1943 | Auzin . |
| 2,564,977 | 8/1951 | Hu . |
| 3,064,310 | 11/1962 | Cooprider ............................... 425/577 |
| 3,670,729 | 6/1972 | Bennett et al. . |
| 3,758,253 | 9/1973 | Pearne ................................... 425/577 |
| 4,000,739 | 1/1977 | Stevens . |
| 4,046,144 | 9/1977 | McFarlane . |
| 4,096,860 | 6/1978 | McLaughlin . |
| 4,198,984 | 4/1980 | Taylor . |
| 4,207,900 | 6/1980 | Patel et al. . |
| 4,299,226 | 11/1981 | Banka . |
| 4,597,756 | 7/1986 | Raible . |
| 4,600,402 | 7/1986 | Rosenbery . |
| 4,619,643 | 10/1986 | Bai . |
| 4,668,225 | 5/1987 | Russo et al. . |
| 4,668,226 | 5/1987 | Omato et al. . |
| 4,723,550 | 2/1988 | Bales et al. . |
| 4,726,374 | 2/1988 | Bales et al. . |
| 4,730,616 | 3/1988 | Frosbie et al. . |
| 4,737,334 | 4/1988 | Folding et al. .......................... 425/438 |
| 4,752,287 | 6/1988 | Kurtz et al. . |
| 4,886,507 | 12/1989 | Patton et al. . |
| 4,887,997 | 12/1989 | Okada . |
| 4,935,008 | 6/1990 | Lewis . |
| 4,969,878 | 11/1990 | Schmidt et al. . |
| 4,995,865 | 2/1991 | Gahara et al. . |
| 5,009,636 | 4/1991 | Wortley . |
| 5,047,021 | 9/1991 | Utterberg . |
| 5,059,186 | 10/1991 | Yamamota et al. . |
| 5,085,645 | 2/1992 | Purdy . |
| 5,225,215 | 7/1993 | Syvrud ................................... 425/577 |
| 5,254,097 | 10/1993 | Schock et al. . |

FOREIGN PATENT DOCUMENTS

62-249721  10/1987  Japan ..................................... 425/577

*Primary Examiner*—Jill L. Heitbrink
*Attorney, Agent, or Firm*—Willian Brinks Hofer Gilson & Lione

[57] ABSTRACT

A method of molding the main body of a Y-adapter that has a straight passageway extending from one extremity to the other and an arcuate passageway that is generated along the arc of a circle. Core pins for the straight and arcuate passageways are placed in a mold such that they merges together to form a single, smooth lumen in the Y-adapter. The arcuate core pin can be withdrawn from the finished Y-adapter as a result of its circular arc.

3 Claims, 2 Drawing Sheets

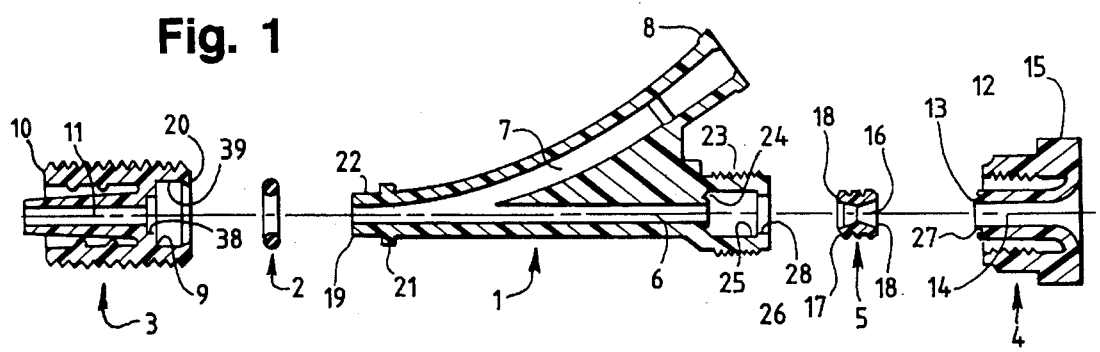
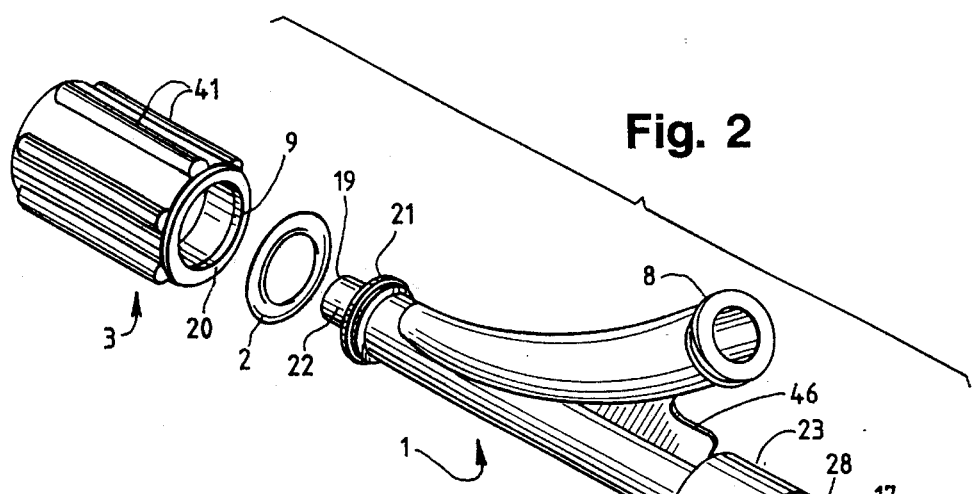
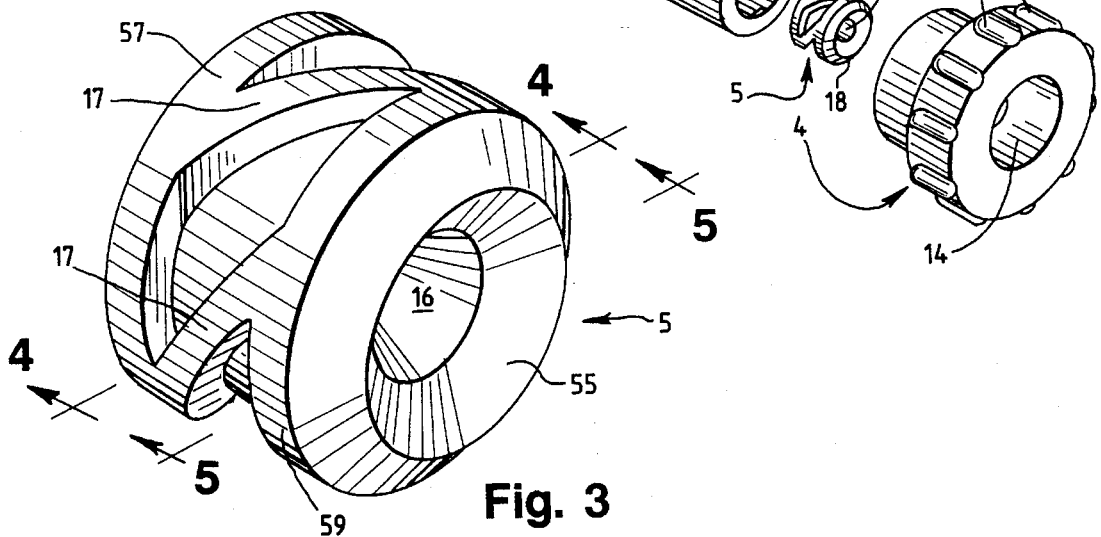

METHOD OF MOLDING Y-ADAPTER WITH A SIDEPORT RADIUS

This application is a division of application Ser. No. 07/935,856, filed Aug. 26, 1992, now U.S. Pat. No. 5,352, 215.

BACKGROUND OF THE INVENTION

The present invention relates to an adapter for use with angioplasty catheters supplying fluid communication and or multiple guide wire introduction that has a hemostasis capability.

In an angioplasty procedure, an accepted and well known medical practice, a catheter is placed into the vascular system of the patient, by first inserting a needle percutaneously into a blood vessel, and then inserting a wire through the needle lumen into the blood vessel, the needle is then removed, a sheath is inserted and the guide catheter is put in place. A guide catheter has a hub at its proximal end from which extends an elongated tubular portion that is open at its distal end. The guide wire is maneuvered and steered through the vascular system until its distal end extends past the area to be treated. With the guide catheter and wire in place, the balloon catheter is threaded through the lumen of the guide catheter. It exits the distal end of the guide catheter at a point approaching the area to be treated. The un-inflated balloon portion of the catheter is located within the artery such that it crosses the stenosis or reduced area. Pressurized inflation fluid is delivered to the inflatable balloon through a lumen formed in the catheter to thus dilate the restricted area. The inflation fluid is generally a liquid and is applied at relatively high pressures. As the balloon is inflated it expands and forces open the stenoses or reduced area of the artery.

Situations are occasionally encountered where it is desirable to utilize more than one dilation catheter and guide wire or more than one guide wire at the same time. An example of such a situation is when there are two or more lesions and it is desired to locate a dilation catheter adjacent to each lesion. In such a situation it may be desirable to dilate the lesions simultaneously thus requiring independent lumens for inflating each balloon. Another example of a situation in which multiple catheters and/or guide wires are desirable is in the situation where the lesion to be treated is close to a branch in the vessel and there is a possibility that dilation of the lesion could cause closure in the adjacent branch. In this situation a guide wire may be placed in the branch not being treated to facilitate getting a catheter to that branch quickly if the need occurs. In any situation in which multiple catheters and/or guide wires are used there are multiple elongated members extending through the vascular system making it even more important that each elongated member is unconstrained and undamaged such that it can be independently manipulated and positioned. The conventional Y-adapter has a main passageway and a branch passageway that joins the main passageway at an acute angle. When a catheter or guide wire is inserted through the branch passageway its first obstacle that must be negotiate is the angle between the main and branch passageways. The lumens forming these passageways are generally straight and intersect at a sharp angle. When a catheter is negotiated through the passageway intersection, it must be forced causing a curved deformation along the catheter shaft. In conventional Y-adapters the catheter is constrained by the internal surfaces of the passageways to a radius of approximately three-quarters of an inch or less. The elastic material from which the catheter is formed resist being bent around such a small radius. The resistance to being bent causes the catheter to be pressed against the internal surface of the passageways. As a result when the catheter is manipulated, twisted, pushed and pulled in an attempt to properly locate its distal end, its movement through the intersection is constrained and the rotational response is compromised. When the catheter is twisted or torqued it tends to wind up, with little or no immediate corresponding movement at the distal end. Then when the torque in the catheter reaches a certain level, it releases and unwinds or whips wildly. When this sudden release occurs the catheter is wildly and violently unwound and is whipped against the lumen walls and against the walls of the vascular system to which it is exposed.

It is a primary objective of the present invention to provide a Y-adapter that can receive a catheter or guide wire through its branch passageway that will merge smoothly into the main passageway and will accommodate the unincumbered manipulation of the catheter or guide wire.

Another objective of the present invention is to provide an adapter with a branch lumen that is arcuate and smoothly merges into the straight lumen of the adapter.

Another objective of the present invention is to provide a manufacturing process for producing the body portion of a Y-adapter that has an arcuate shaped branch lumen.

Still another objective of the present invention is to provide an adapter that has a unique hemo stasis seal at the proximal end of the main port and an arcuate port that smoothly merges into the main port.

These and other objects and advantages of the present invention will no doubt become apparent to those skilled in the art after having read the following detailed description of the preferred embodiment which are contained in and illustrated by the various drawing figures.

SUMMARY OF THE INVENTION

To achieve these and other objectives, the present invention provides a new and unique Y-adapter in which the lumen extending through the side arm is arcuate and smoothly merges into the lumen extending through the central arm.

A preferred embodiment of the present invention includes a Y-adapter in which the lumen extending through the side arm is formed along the arc of a circle.

A preferred embodiment of the hemo stasis seal has a generally tubular shape having spiral ribs formed along its outer surface.

An important advantage of the present invention is that a catheter or guide wire can be smoothly inserted through the side arm of a Y-adapter into the central arm and then twisted and manipulated without distortion.

It is another advantage of the present invention that the arcuate side lumen and straight lumen can be accurately formed in the body portion of the Y-adapter in a molding process.

These and other objects and advantages of the present invention will no doubt become apparent to those skilled in the art after having read the following detailed description of the preferred embodiment which are contained in and illustrated by the various drawing figures.

BRIEF DESCRIPTION OF DRAWING

The novel features which are characteristic of the invention are set forth in the appended claims. The invention itself, together with further objects and advantages will be best understood by reference to the following description of the illustrated embodiment taken in connection with the accompanying drawings, in which:

FIG. 1 is an exploded cross sectional view of the Y-adapter.

FIG. 2 is an exploded perspective view of the Y-adapter.

FIG. 3 is a perspective view of the hemo stasis seal.

DETAILED DESCRIPTION OF THE PREFERRED EMBODIMENT

Figure 5:
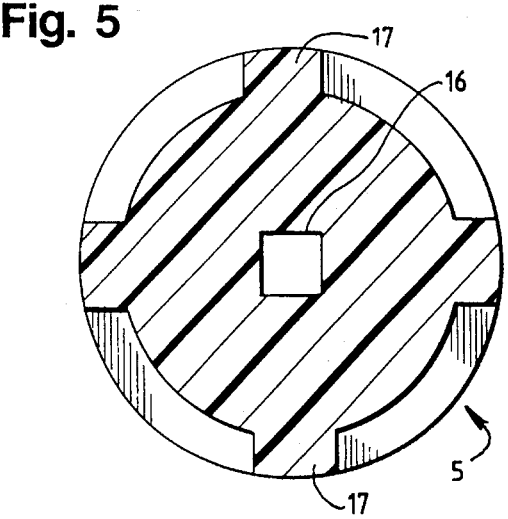
FIG. 5 is a cross sectional view of the hemo stasis seal in its compressed condition.

FIG. 1 illustrates all of the components of the Y-adapter, unassembled but displayed along a dashed line along which the components would be moved in the assembly of the Y-adapter. In FIG. 1 all of the components are shown in cross section views.

Main body 1 is molded from a plastic material such as polycarbonate, or other injection moldable polymer. The main body 1 has a straight port or passageway 6 formed therein extending from the proximal end 26 to the distal end 19. A cylindrical shaped opening 25, having a larger diameter than the straight port or passageway 6, is formed in the main body 1 at its proximal end 26. The O-shaped surface that extends between straight port 6 and the cylindrical shaped opening 25 functions as a seal seat 24 for the hemo stasis seal 5. The cylindrical shaped opening 25 is concentric with the straight port 6 and is also concentric with an outer cylindrical surface having outwardly facing threads 23 formed thereon. There is a continuous under cut 28 formed at the proximal end of the cylindrical shaped opening 25 extending toward the straight port 6.

The main body 1 also has an arching port or passageway 7 formed therein. Arching port or passageway 7 is formed along the arc of a circle generated from a fixed point. The radius of this circle, in the preferred embodiment, being 2.55∓0.50 inches. A standard female luer fitting 8 is formed at the proximal end of the arching port or passageway 7.

Both straight port 6 and arching port 7 have circular cross sections and both have a slight taper along their length. Both ports 6 and 7 have a larger diameter at their proximal ends then at their distal ends. The purpose of this taper relates to the manufacturing process for the main body 1 which will be discussed in more detail with regard to FIGS. 6–9.

The main body 1 has an external outer cylindrical surface at its distal end 19 that functions as a seat 22 for the o-ring 2. A collar is formed on the main body 1 adjacent the o-ring seat 22 that has a snap ring 21 along its outer periphery.

The swivel male luer 3 is molded from a plastic material such as polycarbonate. A cylindrical bore 39 is formed in the proximal end of the swivel male luer 3 that functions as an o-ring seat 9.

The o-ring 2 is a standard 0-ring made from elastomeric material such as silicone.

The swivel male luer 3 has a cylindrical bore 38 that is of a smaller diameter than cylindrical bore 39 formed concentric with bore 39 that functions to receive the distal end 19 of the main body 1. A standard male luer is formed at the distal end 10 of the swivel male luer 3. A thru hole 11 is formed through the center of the swivel male luer 3 that is aligned with the straight port 6 of the main body 1 when the swivel male luer 3 is assembled on the main body 1. There is a continuous under cut 20 formed around the periphery of the large cylindrical bore 39 that extends toward the axis of thru hole 11. In assembling the swivel male luer 3 and main body 1 the o-ring 2 is inserted into the 0-ring seat 9 and the distal end 19 of the main body 1 is inserted into the proximal end of the swivel male luer 3 such that o-ring seat 22 extends through the 0-ring 2 and the distal end 19 extends into the small cylindrical bore 38. The main body 1 is then forced into the swivel male luer 3, compressing 0-ring 2 between 0-ring seat 9 and 0-ring seat 22 until snap ring 21 passes through the under cut 20. Upon release of the pressure, on the main body 1 and swivel male luer 3, the elasticity of the 0-ring 2 will exert a pressure on main body 1 in a direction to separate swivel male luer 3 from main body 1. However, separation will be prevented by the interaction of the under cuts 20 and the snap ring 21. When this assembly has been completed a seal is formed between the main body 1 and the swivel male luer 3. Swivel male luer 3 can however swivel with respect to the main body 1. The Y-adapter can be connected by the standard male luer to other equipment, for example a guide catheter (not shown).

The thumb screw 4 is molded from plastic material, for example polycarbonate. The thumb screw 4 has a thru port 14 extending centrally therethrough which is flared outwardly at its proximal end. A cylindrical shaped groove, concentric with thru port 14, is formed in the distal end of thumb screw 4. On the outer surface of this cylindrical shaped groove there are inwardly facing threads 12 that match the outwardly facing threads 23 of the main body 1. A seal seat 13 is formed between the cylindrical shaped groove and the thru port 14 for a purpose to be discussed later in the specification. A snap ring 27 is formed along the outer periphery of the seal seat 13 extending toward the inwardly facing threads 12 that cooperates with the under cut 28 of the main body 1 to prevent unintentional release of the thumb screw 4 from the main body 1. There are a plurality of outwardly facing ribs 15 formed along the outer periphery of the thumb screw 4 for the purpose of making it easier to grip the thumb screw 4 between a finger and the thumb. The outwardly facing ribs 15 are also shown in FIG. 2.

The hemo stasis seal 5 is formed of elastomeric material, for example silicone. There is a thru hole 16 extending centrally of hemo stasis seal 5 that has distal and proximal sealing facings 18 at its extremities. There are a plurality of rotational limiting ribs 17 formed along the outer surface of the hemo stasis seal 5.

After locating the hemo stasis seal 5 in the cylindrical shaped opening 25 formed in the proximal end of the main body 1 the thumb screw 4 is assembled to the main body 1 by inserting the distal end of the thumb screw 4 into the cylindrical opening 25 such that the snap ring 27 extends past the under cut 28 of the main body 1. The purpose of the under cut 28 and snap ring 27 is to prevent the unintentional disconnection of the thumb screw 4 from the main body 1 when the inwardly facing threads 12 of the thumb screw 4 are no longer in engagement with the outwardly facing threads 23 of the main body 1. After the snap ring 27 has passed through the under cut 28 engagement of outwardly facing threads 23 and inwardly facing threads 12 begin. The thumb screw 4 is rotated in the clockwise direction to advance the thumb screw 4 toward the distal end 19 of the main body 1.

As the thumb screw 4 advances toward the distal end 19 of the main body 1 the seal seat 13 of the thumb screw 4 engages the proximal sealing face 18 of the hemo stasis seal 5, the distal sealing facing 18 of the hemo stasis seal 5 engages the seal seat 24 of the main body 1 and the outer surfaces of the rotational limiting ribs 17 engage the cylindrical surface of the cylindrical opening 25. Further rotation of the thumb screw 4 in the clockwise direction causes the hemo stasis seal 5 to be deformed and the thru hole 16 is compressed around an elongated element, for example a guide wire, that is extending therethrough thus forming a hemo stasis seal around the guide wire.

FIG. 2 is a perspective view of the components that form the Y-adapter. The individual components are shown separated so that more of each component is visible. The components are aligned along an axis (not shown) that extends through the center of the straight port 6 of the main body 1. FIG. 2 supplements the understanding of the structure of the Y-adapter as described with reference to FIG. 1 since some elements of various components are better depicted in this perspective view than in the cross sectional view of FIG. 1. For example there are a plurality of outwardly facing ribs 41 on the swivel male luer 3 that are helpful in swiveling the male luer 3 with respect to the main body 1 and in connecting the swivel male luer 3 to other equipment such as a guide catheter. Also the stabilizing web 64 between the straight and arcuate passageways is seen in this view as well as the outwardly facing ribs 15 on the thumb screw 4.

FIG. 3 is a perspective view of the hemo stasis seal 5 that is similar but larger then the illustration of this component in FIG. 2. It can be seen in FIG. 3 that the hemo stasis seal 5 has an upstanding ring 57 at its distal end and another upstanding ring 59 at its proximal end. The rings 57 and 59 are connected by the plurality of rotational limiting ribs 17. The height of the rings 57, 59 and the rotational limiting ribs 17 are the same and their outer surfaces form the outer surface of the hemo stasis seal 5. It should also be noted that frusta conical depressions 55 are formed in the distal and proximal sealing facings 18 of the hemo stasis seal 5.

Figure 4:
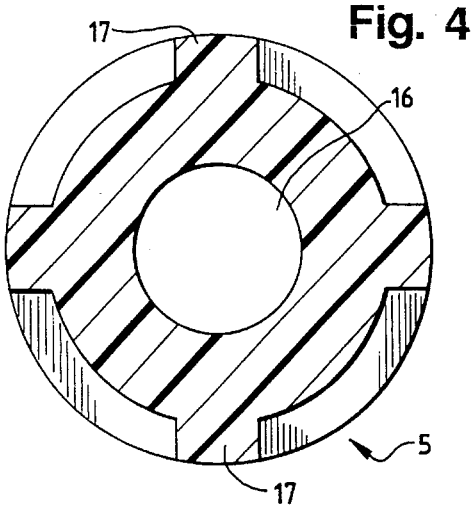
FIG. 4 is a cross sectional view of the hemo stasis seal in its un-compressed condition.

FIG. 4 is a cross section view taken along the central portion of the hemo stasis seal 5, when the seal is relaxed and not compressed. In this view the thru hole 16 is at its maximum size.

FIG. 5 is a cross section view taken along the central portion of the hemo stasis seal 5, when the seal is under tension and compressed. In this view the thru hole 16 is shown reduced considerably from its maximum size as seen in FIG. 4.

Figure 6:
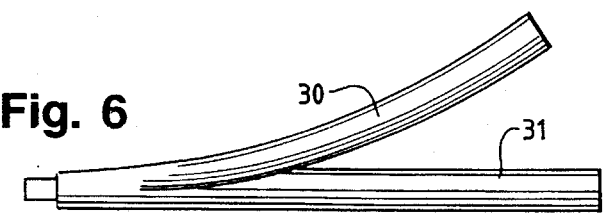
FIG. 6 is a plan view of combined arcuate tapering core pin interfacing with the straight tapering core pin.
Figure 7:
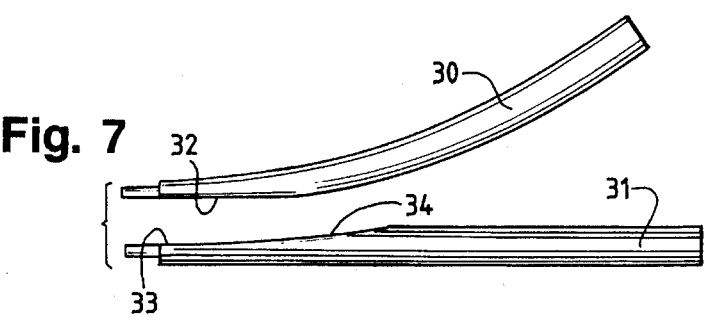
FIG. 7 is an exploded plan view of core pins.
Figure 8:
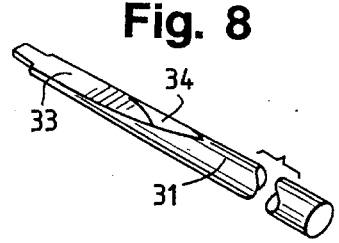
FIG. 8 is a perspective view of the straight tapering core pin.

FIG. 6 is a plan view of the pins or cores 30 and 31 that are used to develop the straight port or passageway 6 and the arching port or passageway 7 when molding the main body 1. The arching and tapering pin or core 30 is used to form the arching port 7. Pin 30 is curved along the arc of a circle and is tapered slightly such that its cross sectional diameter is larger at the proximal end than at the distal end. In the preferred embodiment the radius of the arc for pin 30 is $2.55 \mp 0.25$ inches. In FIG. 6 the pins 30 and 31 are shown nestled together. In FIG. 7 pins 30 and 31 are shown separated from each other. As can be best seen in FIG. 7 pin 30 is cut flat on mold shut off surface 32.

Straight tapering pin 31, shown separated from pin 30 in FIG. 7, has a corresponding mold shut off surface. The mold shut off surface of pin 31 has a flat mold shut off surface 33 as well as a contoured mold shut off surface 34. The flat mold shut off surface 33 of pin 31 has the identical shape as the mold shut off surface 32 of pin 30 and the two surfaces fit flush together. The contoured mold shut off surface 34 of pin 31 is designed to match the outer surface of pin 30 so that the pins 30 and 31 can nestle closely together such that there will be no gaps along the intersection of the pins. The flat 33 and contoured 34 mold shut off surfaces of pin 31 can be best seen in the perspective view of FIG. 8. Pin 31 is slightly tapered such that it has a larger diameter at its proximal end then at its distal end.

Figure 9:
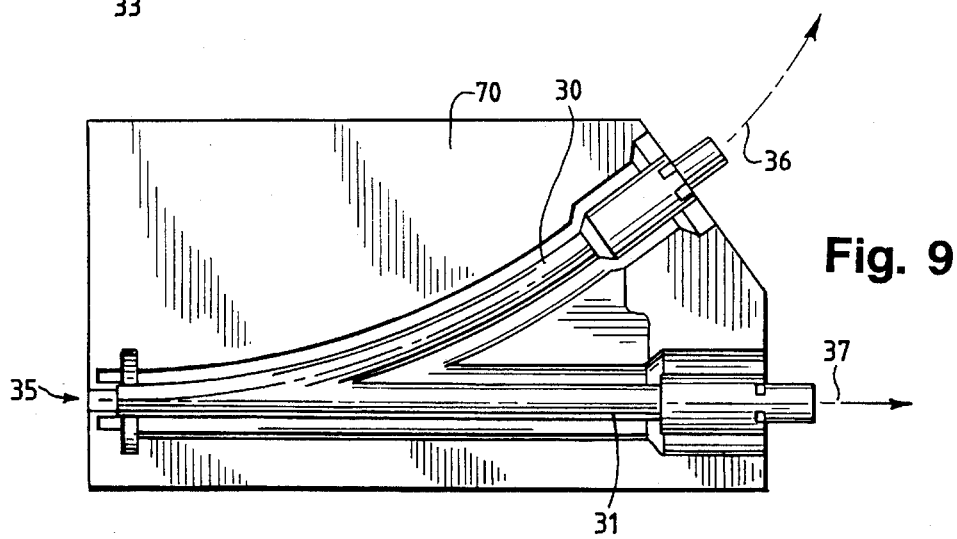
FIG. 9 is a mold for forming the body portion of the Y-adapter.

Referring now to FIG. 9 wherein a part of the mold cavity block 70 is shown. The pins 30 and 31 are placed in the mold cavity prior to performing the molding operation and are supported by the cavity block 70 such that after the main body has been molded both ends of pins 30 and 31 are accessible from outside the molded main body. The plastic material from which main body 1 is made is injected into the mold and completely surrounds the pins 30 and 31. When the pins 30 and 31 are removed the main body has ports or passageways 6 and 7 that correspond in shape and size to the pins 30 and 31. The mold for main body 1 is designed such that after the molding process is completed the proximal and distal ends of the pins 30 and 31 are accessible through openings formed in the molded main body 1. The pins 30 and 31 are removed from the molded main body, for example, by exerting a force on the pins 30 and 31. The force can be a pushing force, represented by arrow 35 in FIG. 9 on the distal ends of pins 30 and 31, a pulling force, represented by arrows 36 and 37 in FIG. 9 on the proximal ends of pins 30 and 31 simultaneously exerting pushing 35 and pulling forces 36 and 37. As previously stated the pins 30 and 31 are slightly tapered, having a larger cross sectional diameter at their proximal ends than at their distal ends. By so tapering the pins and directing the force to remove the pins such that the larger cross sectional end of the pins are the leading ends and the smaller cross sectional ends are the trailing ends, facilitates the removal of pins 30 and 31 from the molder main body 1.

The design of port 7 along the arc of a circle makes it possible to remove pin 30 from the molded main body 1. As pin 30 is being removed from the main body 1 it moves along an arc generated about the pins center. If pin 30 had a non circular curve it would be locked in the molded main body 1.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method of molding the main body for a Y-adapter that has a straight passageway extending from one extremity to the other and an arcuate branch passageway that smoothly merges into the straight passageway including the step of:

(a) providing a mold for the main body that includes means for supporting a straight core pin and an arcuate core pin, said straight and arcuate core pins each include corresponding mold shut off surfaces that interface with each other such that a single, smooth passageway is formed in the main body and such that after the main body has been molded the proximal and distal ends of the straight and arcuate core pins are accessible from outside of the molded main body, (b) placing the straight and arcuate core pins in the mold prior to injecting the material, from which the main body is to be formed, into the mold;

(c) injecting the material from which the main body is to be formed into the mold; and (d) exerting force on the straight and arcuate cores causing them to slide out of the molded main body.

2. The method as set forth in claim 1 wherein the arcuate core pin is generated along the arc of a circle.

3. The method as set forth in claim 1 wherein the radius of the circle is 2.55 plus or minus 0.50 inches.

\* \* \* \* \*

UNITED STATES PATENT AND TRADEMARK OFFICE
CERTIFICATE OF CORRECTION

PATENT NO.  : 5,470,522
DATED       : November 28, 1995
INVENTOR(S) : Scott P. Thome et al.

It is certified that error appears in the above-indentified patent and that said Letters Patent is hereby corrected as shown below:

<u>On the Title Page</u>

In column 2, line 5 of the "ABSTRACT", delete "merges" and substitute --merge--.

<u>In the Claims</u>
Col. 8, line 26:

In claim 3, line 1, delete "1" and substitute --2--.

Signed and Sealed this

Eleventh Day of June, 1996

*Attest:*

BRUCE LEHMAN

*Attesting Officer*     *Commissioner of Patents and Trademarks*